United States Patent [19]

Umezawa et al.

[11] Patent Number: 4,499,083

[45] Date of Patent: Feb. 12, 1985

[54] 3-O-DEMETHYL DERIVATIVES OF THE ISTAMYCIN B SERIES OF COMPOUNDS

[75] Inventors: Hamao Umezawa; Yoshiro Okami, both of Tokyo; Shinichi Kondo, Yokohama, all of Japan

[73] Assignee: Zaidan Hojin Biseibutsu Kagaku Kenkyu Kai, Tokyo, Japan

[21] Appl. No.: 298,844

[22] Filed: Sep. 3, 1981

[30] Foreign Application Priority Data

Sep. 11, 1980 [JP] Japan ................ 55-125334

[51] Int. Cl.$^3$ .............. A61K 31/71; C07H 15/22
[52] U.S. Cl. .................. 514/36; 536/16.8; 536/17.9; 536/16.1
[58] Field of Search ............ 536/4, 17 R, 16.8, 16.1; 424/180

[56] References Cited

U.S. PATENT DOCUMENTS

| | | | |
|---|---|---|---|
| 4,242,503 | 12/1980 | Lartey et al. | 536/17 R |
| 4,255,421 | 3/1981 | Watanabe et al. | 536/17 R |
| 4,283,529 | 8/1981 | Rosenbrook, Jr. | 536/17 R |
| 4,296,106 | 10/1981 | Umezawa et al. | 536/17 R |
| 4,330,673 | 5/1982 | Rosenbrook, Jr. | 536/17 R |
| 4,382,926 | 5/1983 | Umezawa et al. | 421/181 |

FOREIGN PATENT DOCUMENTS 2048855  12/1980  United Kingdom ............ 536/17 R

OTHER PUBLICATIONS

Egan et al., "Jour. Antibiotics", vol. 30, No. 7, 1977, pp. 552–562.
Deushi et al., "Jour. Antibiotics", vol. 32, No. 3, pp. 187–192, 1979.
Watanabe et al., "Jour. Antibiotics", vol. 32, No. 10, 1979, pp. 1066–1068.
Deushi et al., "Jour. Antibiotics", vol. 33, No. 11, 1980, pp. 1274–1280.
Ikeda, "Jour. Antibiotics", vol. 33, No. 11, pp. 1281–1288.
Horiuchi et al., "Jour. Antibiotics", vol. 33, No. 12, pp. 1577–1580.

*Primary Examiner*—Johnnie R. Brown
*Attorney, Agent, or Firm*—Richard R. Lloyd

[57] ABSTRACT

New derivatives of the istamycin B series of compounds are provided, which are 3-O-demethylistamycin $B_O$, 3-O-demethylistamycin B and 3-O-demethyl-2''-N-formimidoylistamycin B represented generally by Formula I or specifically by Formulae Ia, Ib and Ic, respectively. Compound Ia is useful as an intermediate for the preparation of Compounds Ib and Ic and the latter two compounds exhibit a high antibacterial activity against a wide variety of Gram-positive and Gram-negative bacteria and are useful antibiotics. Also provided are processes for the preparation of the new derivatives starting from istamycin $B_O$.

5 Claims, No Drawings

3-O-DEMETHYL DERIVATIVES OF THE ISTAMYCIN B SERIES OF COMPOUNDS

SUMMARY OF THE INVENTION

This invention relates to new compounds of the istamycin B series, more particularly 3-O-demethylistamycin $B_O$, 3-O-demethylistamycin B and 3-O-demethyl-2''-N-formimidoylistamycin B which are useful as semisynthetic aminoglycosidic antibiotics, and to their preparation.

BACKGROUND OF THE INVENTION

We have previously discovered a new strain of actinomycetes, *Streptomyces tenjimariensis* SS-939 which was deposited in the Japanese public depository "Fermentation Research Institute" under the deposit number FERM-P 4932 and in the American Type Culture Collection under ATCC Number 31603, and produced by cultivation of said strain several different new aminoglycosidic antibiotic substances, istamycin A, istamycin B, istamycin $A_O$ and istamycin $B_O$ (refer to our Japanese Patent KOKAI No. 145697/80 and No. 43295/81; our published U.K. Patent Application GB 2,048,855A; and our allowed U.S. patent application Ser. No. 141,492, filed Apr. 18, 1980, now U.S. Pat. No. 4,296,106). Subsequently, we totally synthesized di-$N^{6'},O^3$-demethylistamycin A and found its antibacterial activity against *Pseudomonas aeruginosa* to be significantly higher than that of istamycin A (refer to Japanese Patent Application No. 38889/80; U.K. Patent Application 8108886; U.S. patent application Ser. No. 241,649, now abandoned). We than continued our studies on istamycin antibiotics with the intention of converting istamycin B (which has a higher antibacterial activity than istamycin A) into the 3-O-demethyl derivative thereof, and have now succeeded in synthesizing 3-O-demethylistamycin B starting from istamycin $B_O$, and have found that 3-O-demethylistamycin B is effective against not only *Pseudomonas aeruginosa* but also a variety of resistant bacteria. In this series of studies, we have also synthesized 3-O-demethylistamycin $B_O$ and 3-O-demethyl-2''-N-formimidoylistamycin B, the former being useful as an intermediate to be converted into 3-O-demethylistamycin B by glycylating the 4-methylamino group thereof, and the latter being a 3-O-demethylistamycin B derivative useful as an antibiotic similarly to formimidoylistamycin B and formimidoylistamycin A (see Japanese Patent Application No. 41184/80; Japanese Patent Application No. 107201/80; U.K. Patent Application No. 8108602; and U.S. patent application Ser. No. 244,232, now U.S. Pat. No. 4,382,926) both of which were synthesized by us.

The 3-O-demethylistamycin $B_O$, 3-O-demethylistamycin B and 3-O-demethyl-2''-N-formimidoylistamycin B described and claimed herein have been disclosed by us in J. Antibiotics, 33, 1577-1580 (December 1980), along with details of their preparation and their antibacterial activity.

We are aware of U.S. Pat. No. 4,255,421 which discloses certain O-demethylaminoglycosides and claims those of the formula

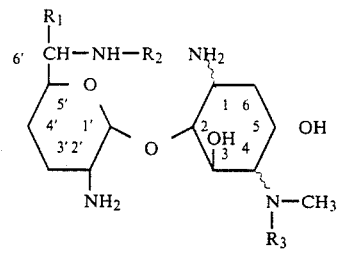

wherein $R_1$ and $R_2$ are the same or different and are hydrogen or methyl, $R_3$ is hydrogen or an unsubstituted or substituted aminoacyl group having 2 to 4 carbon atoms in the acyl moiety, the substituent being selected from hydroxy, formyl and carbamoyl; provided that, when $R_1$, $R_2$ and $R_3$ are each hydrogen atoms, the methylamino group at the 4-position is not oriented trans to the hydroxyl groups at the 3- and 5-positions.

Although the aminocyclitol rings are numbered in the opposite directions in U.S. Pat. No. 4,255,421 and in the compounds disclosed and claimed herein (compounds named as 3-O-demethyl derivatives herein are named as 5-O-demethyl derivatives therein), it may be seen that the claims of U.S. Pat. No. 4,255,421 literally include within their scope two of the three compounds disclosed and claimed herein, i.e. 3-O-demethylistamycin $B_O$ and 3-O-demethylistamycin B. However, U.S. Pat. No. 4,255,421 does not exemplify either of these two compounds and, further, neither discloses the starting material necessary for their preparation nor teaches how the necessary starting material may be prepared. Thus, 3-O-demethylistamycin $B_O$ and 3-O-demethylistamycin B contain a 6'-N-methyl group and a C-1 amino group which is cis to the sugar moiety, and the starting material for the demethylation reaction (istamycin $B_O$ herein) must contain these same groups and configurations. U.S. Pat. No. 4,255,421, on the other hand, discloses as starting materials only antibiotic complex KA-6606 [the sporaricins; see J. Antibiotics, 32, 187 (1979)], at least some of which contain a C-1 amino group that is cis to the sugar moiety, but all of which have a 6'-C-methyl group; antibiotic complex KA-7038 [the sannamycins; see J. Antibiotics, 32, 1066 (1979)], some of which contain a 6'-N-methyl group but all of which have a C-1 amino group which is trans to the sugar moiety; and fortimicins A and B [see J. Antibiotics, 30, 552 (1977)], both of which have a 6'-C-amino group and a C-1 amino group which is trans to the sugar moiety, as well as an additional hydroxyl group on the C-6 position (numbered C-2 herein) which is not present in the compounds claimed herein. Thus, the sporaricin, sannamycin and fortimicin starting materials disclosed in U.S. Pat. No. 4,255,421 are not suitable starting materials for the preparation of any of the three compounds disclosed and claimed herein, since they have the wrong 6'-substitution and/or the wrong stereo configuration of the 1-amino group, and in some instances have an additional hydroxyl group on the C-6 position. The starting materials disclosed in U.S. Pat. No. 4,255,421 are products of fermentation and not synthetic products, and there is no disclosure of how to obtain the necessary starting materials for the preparation of the compounds disclosed and claimed herein. Thus, U.S. Pat. No. 4,255,421 does not contain an enabling disclosure for the preparation of the herein claimed 3-O-demethylistamycin $B_O$, 3-O-demethylistamycin B or 3-O-demethyl-2''-N-formimidoylistamycin B.

DETAILED DESCRIPTION OF THE INVENTION

According to a first aspect of this invention, therefore, there are provided as new compounds 3-O-demethyl derivatives of istamycin B series compounds of formula I:

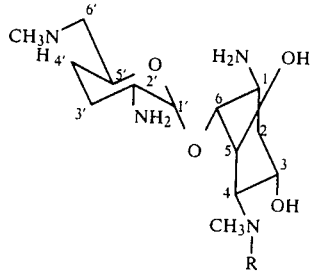

wherein R represents a hydrogen atom, a glycyl group or an N-formimidoylglycyl group, and acid addition salts thereof. Concretely, the following three compounds and their acid addition salts are provided:

3-O-Demethylistamycin $B_O$ (R is H)
3-O-Demethylistamycin B $$2'' \quad 1''$$
(R is $H_2NCH_2CO-$)

3-O-Demethyl-2''-N-formimidoylistamycin B $$2'' \quad 1''$$
(R is $HN=CHNHCH_2CO-$).

Physico-chemical properties of the new compounds according to this invention are shown in Table 1.

TABLE 1

| | Physico-chemical properties | | |
|---|---|---|---|
| | 3-O—Demethyl-istamycin $B_0$.dicarbonate | 3-O—Demethyl-istamycin B.3/2 carbonate | 3-O—Demethyl-2''-N—formimidoylistamycin B.disulphate.trihydrate |
| Appearance | Colorless powder | Colorless powder | Colorless powder |
| Decomposition point | 122–126° C. | 182–184° C. | 240° C. (with foaming) (gradually colored from about 210° C.) |
| Specific rotation | $[\alpha]_D^{25} +129°$ (c 1, $H_2O$) | $[\alpha]_D^{25} +130°$ (c 1, $H_2O$) | $[\alpha]_D^{26} +85°$ (c 1, $H_2O$) |
| Elemental analysis (%) | *1 | *2 | *3 |
| C | 43.07 (43.43) | 44.42 (44.86) | 31.27 (31.28) |
| H | 7.40 (7.75) | 7.55 (7.75) | 6.74 (6.79) |
| N | 12.65 (12.66) | 14.65 (14.95) | 12.14 (12.87) |
| S | — | — | 9.72 (9.82) |
| Mass spectrometry | m/e 319 (M + 1)$^+$ | m/e 376 (M + 1)$^+$ | — |
| Cellulose-thin layer chromatography | | | |
| Rf*4 | 0.51 (single spot) | 0.37 (single spot) | 0.29 (single spot) |

*1 Calculated values for $C_{14}H_{30}N_4O_4.2H_2CO_3$
*2 Calculated values for $C_{16}H_{33}N_5O_5.3/2H_2CO_3$
*3 Calculated values for $C_{17}H_{34}N_6O_5.2H_2SO_4.3H_2O$
*4 Solvent system: propanol-pyridine-acetic acid-water (15:10:3:12 by volume); ninhydrin color reagent The antibacterial spectra of 3-O-demethylistamycin B.sesquicarbonate and 3-O-demethyl-2''-N-formimidoylistamycin B.disulphate.trihydrate are shown in Table 2, along with that of istamycin B for comparison purposes.

TABLE 2

| | Antibacterial spectra | | |
|---|---|---|---|
| | Minimum inhibitory concentrations (mcg/ml)*1 | | |
| Test microorganisms | 3-O—Demethyl-*2 istamycin B | 3-O—Demethyl-2''-*3 N—formimidoylistamycin B | Istamycin B |
| *Staphylococcus aureus* FDA 209P | 0.39 | 0.20 | 0.39 |
| *Staphylococcus aureus* Smith | <0.20 | <0.20 | <0.20 |
| *Staphylococcus aureus* Ap01 | 0.78 | 0.78 | 0.78 |
| *Staphylococcus epidermidis* 109 | 0.78 | 0.78 | 0.78 |
| *Micrococcus flavus* FDA 16 | 3.13 | <0.20 | 6.25 |
| *Sarcina lutea* PCI 1001 | 0.39 | <0.20 | 0.20 |
| *Bacillus anthracis* | <0.20 | <0.20 | <0.20 |
| *Bacillus subtilis* PCI 219 | <0.20 | <0.20 | <0.20 |
| *Bacillus subtilis* NRRL B-558 | <0.20 | <0.20 | <0.20 |
| *Bacillus cereus* ATCC 10702 | 1.56 | 1.56 | 1.56 |
| *Corynebacterium bovis* 1810 | 1.56 | 0.78 | 0.78 |
| *Mycobacterium smegmatis* ATCC 607 | <0.20 | <0.20 | 0.78 |
| *Escherichia coli* NIHJ | 1.56 | 1.56 | 1.56 |
| *Escherichia coli* K-12 | 3.13 | 1.56 | 1.56 |
| *Escherichia coli* K-12 R5 | 6.25 | 3.13 | 3.13 |
| *Escherichia coli* K-12 R388 | 1.56 | 1.56 | 1.56 |
| *Escherichia coli* K-12 J5R11-2 | 1.56 | 1.56 | 1.56 |

TABLE 2-continued

| | Antibacterial spectra | | |
| | Minimum inhibitory concentrations (mcg/ml)[*1] | | |
| Test microorganisms | 3-O—Demethyl-[*2] istamycin B | 3-O—Demethyl-2"-[*3] N—formimidoylistamycin B | Istamycin B |
| --- | --- | --- | --- |
| Escherichia coli K-12 ML1629 | 3.13 | 1.56 | 1.56 |
| Escherichia coli K-12 ML1630 | 3.13 | 1.56 | 1.56 |
| Escherichia coli K-12 ML1410 | 3.13 | 3.13 | 3.13 |
| Escherichia coli K-12 ML1410 R81 | 3.13 | 1.56 | 1.56 |
| Escherichia coli K-12 LA290 R55 | 6.25 | 1.56 | 3.13 |
| Escherichia coli K-12 LA290 R56 | 3.13 | 1.56 | 1.56 |
| Escherichia coli K-12 LA290 R64 | 3.13 | 1.56 | 1.56 |
| Escherichia coli W677 | 1.56 | 0.78 | 1.56 |
| Escherichia coli JR66/W677 | 6.25 | 3.13 | 3.13 |
| Escherichia coli K-12 C600 R135 | 6.25 | 12.5 | 12.5 |
| Escherichia coli JR255 | 1.56 | 0.78 | 0.78 |
| Klebsiella pneumoniae PCI602 | 3.13 | 1.56 | 1.56 |
| Klebsiella pneumoniae 22#3038 | 6.25 | 3.13 | 3.13 |
| Shigella dysenteriae JS11910 | 6.25 | 3.13 | 3.13 |
| Shigella flexneri 4B JS11811 | 6.25 | 3.13 | 3.13 |
| Shigella sonnei JS11746 | 6.25 | 3.13 | 3.13 |
| Salmonella typhi T-63 | 1.56 | 0.78 | 0.39 |
| Salmonella enteritidis 1891 | 3.13 | 1.56 | 1.56 |
| Proteus vulgaris OX19 | 0.78 | 0.39 | 0.39 |
| Proteus rettgeri GN311 | 12.5 | 12.5 | 12.5 |
| Proteus rettgeri GN466 | 6.25 | 3.13 | 6.25 |
| Serratia marcescens | 12.5 | 3.13 | 6.25 |
| Serratia sp. SOU | 25 | >100 | 100 |
| Serratia sp. 4 | 12.5 | 6.25 | 50 |
| Providencia sp. Pv16 | 25 | 25 | 6.25 |
| Providencia sp. 2991 | 12.5 | 12.5 | 6.25 |
| Pseudomonas aeruginosa A3 | 3.13 | 1.56 | 6.25 |
| Pseudomonas aeruginosa No. 12 | 12.5 | 12.5 | 100 |
| Pseudomonas aeruginosa H9 | 25 | 12.5 | 50 |
| Pseudomonas aeruginosa H11 | 25 | 25 | 50 |
| Pseudomonas aeruginosa TI-13 | 12.5 | 6.25 | 25 |
| Pseudomonas aeruginosa GN315 | 12.5 | 6.25 | 50 |
| Pseudomonas aeruginosa 99 | 25 | 100 | >100 |
| Pseudomonas aeruginosa B-13 | 50 | >100 | >100 |
| Pseudomonas aeruginosa 21-75 | 50 | 25 | 100 |
| Pseudomonas aeruginosa PST1 | 50 | 25 | 100 |
| Pseudomonas aeruginosa ROS 134/PU21 | 50 | 50 | >100 |
| Pseudomonas aeruginosa K-Ps 102 | 6.25 | 12.5 | 50 |
| Pseudomonas maltophilia GN 907 | >100 | >100 | >100 |

[*1]Determined according to a standard serial dilution method on nutrient agar plates which were incubated at 37° C. for 17 hours.
[*2]In the form of sesquicarbonate
[*3]In the form of disulphate.trihydrate The antibacterial spectra data given above clearly demonstrate that 3-O-demethylistamycin B and 3-O-demethyl-2"-N-formimidoylistamycin B exhibit a high antibacterial activity against a wide variety of Gram-negative and Gram-positive bacteria. On the other hand, 3-O-demethylistamycin $B_O$ has a poor antibacterial activity, but is useful as an intermediate for the preparation of 3-O-demethylistamycin B.

3-O-Demethylistamycin $B_O$ (dicarbonate), 3-O-demethylistamycin B (sesquicarbonate) and 3-O-demethyl-2"-N-formimidoylistamycin B (disulphate.trihydrate) are further characterized by their low toxicity. Thus, when the acute toxicity of these three compounds was estimated by intravenous injection in mice, it was found that all the mice tested tolerated a dose of 160 mg/kg of each compound.

3-O-Demethylistamycin $B_O$, 3-O-demethylistamycin B and 3-O-demethyl-2"-N-formimidoylistamycin B according to this invention may be obtained in the form of the free base, a hydrate or a carbonate thereof, and more preferably in view of their stability they can be converted into a pharmaceutically acceptable acid addition salt thereof by reacting with a pharmaceutically acceptable acid in a usual manner. Examples of the pharmaceutically acceptable acids are inorganic acids such as hydrochloric, hydrobromic, sulfuric, phosphoric and nitric acids and organic acids such as acetic, malic, citric, ascorbic and methanesulfonic acids. The compounds may also exist as salt-hydrates, e.g. 3-O-demethyl-2"-N-formimidoylistamycin B.disulfate.trihydrate.

3-O-Demethylistamycin $B_O$ of formula Ia:

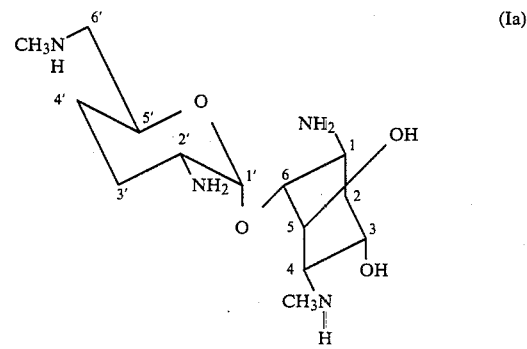

(Ia)

may be prepared according to this invention by demethylating at the 3-methoxy group of istamycin $B_O$ of formula II:

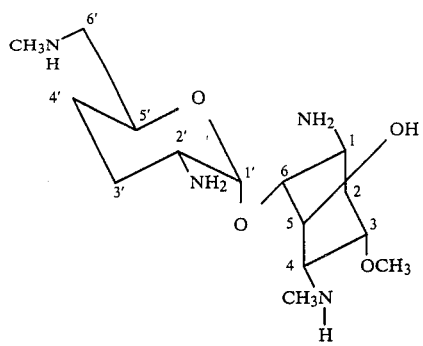

in a manner known per se. There are several processes wellknown in the art for demethylation of the methoxy group, such as treatment with hydriodic acid or hydrobromic acid, treatment with a Lewis acid, typically a metal halide such as aluminium trichloride, aluminium tribromide, boron trichloride, boron tribromide, boron trifluoride, zinc dichloride, zinc diiodide or iron trichloride, or treatment with an alkali metal such as sodium or lithium (see "The Chemistry of the Ester Linkage", edited by S. Patai, page 21, published by Interscience Publishers Inc. in 1967). A preferred process for the demethylation reaction to be used here is one wherein istamycin B$_O$ is heated with 48% hydrobromic acid at 90°–100° C. in a sealed tube, which can achieve effective demethylation reaction in a short reaction time as described in U.K. Application GB No. 2 037 743.

3-O-Demethylistamycin B of formula Ib:

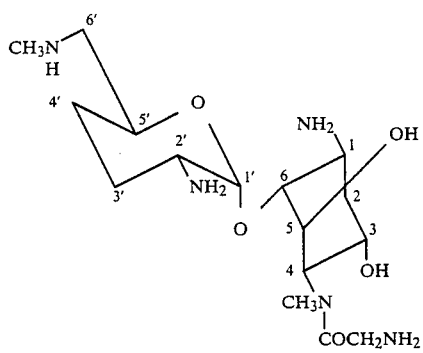

may be prepared according to this invention by acylating the 4-methylamino group of 3-O-demethylistamycin B$_O$ of formula Ia with glycine. In practice, this is attained by previously protecting the 1- and 2'-amino groups and the 6'-methylamino group of 3-O-demethylistamycin B$_O$ with a conventional monovalent amino-protecting group to give a 1-, 2'- and 6'-N-protected derivative of 3-O-demethylistamycin B$_O$ of Formula III:

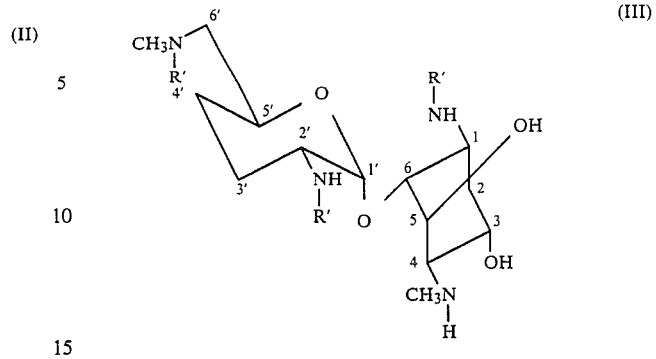

wherein R' represents a conventional monovalent amino-protecting group, reacting the compound of Formula (III) with a conventionally N-protected glycine whose amino-protecting group is the same as or different from those on the 1-, 2'- and 6'-positions of the compound of Formula (III), or with a reactive derivative thereof, in an inert solvent, at a temperature of from about 0° C. to about 100° C., to acylate the 4-methylamino group, thus forming a compound of Formula IV:

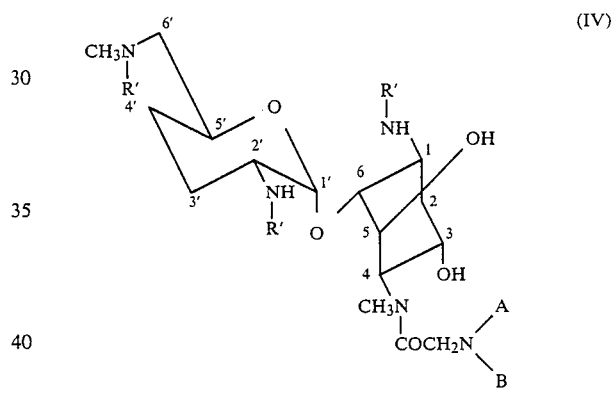

wherein R' has the same meaning as defined above, A represents a hydrogen atom and B represents a conventional monovalent amino-protecting group or A and B together form a conventional divalent amino-protecting group, and then removing all the amino-protecting groups on the compound of Formula IV by conventional means to give 3-O-demethylistamycin B of Formula Ib.

In the amino-protection step, the 1- and 2'-amino groups and the 6'-methylamino group of 3-O-demethylistamycin B$_O$ of Formula Ia may be simultaneously protected with a monovalent amino-protecting group without affecting the 4-methylamino group thereof. As an example of a suitable, conventional monovalent amino-protecting group, there may be mentioned an alkoxycarbonyl group, particularly having 2–7 carbon atoms, such as tert-butoxycarbonyl and tert-amyloxycarbonyl; a cycloalkyloxycarbonyl group, particularly 4–7 carbon atoms such as cyclohexyloxycarbonyl; an aralkyloxycarbonyl group such as benzyloxycarbonyl; and an acyl group, particularly an alkanoyl group having 2–7 carbon atoms such as trifluoroacetyl and o-nitrophenoxyacetyl. The introduction of such an amino-protecting group may be carried out in a manner known in the syntheses of peptides, e.g. by using a known amino-protecting group-introducing reagent in the form of an acid halide, an acid azide, an active ester, an acid anhydride, etc. By using such an amino-protecting group-introducing reagent in an amount of 2.5-4.0 moles per mole of 3-O-demethylistamycin B$_O$, it is possible to preferentially form 1,2',6'-tri-N-protected 3-O-demethylistamycin B$_O$ of formula III above due to the difference in reactivity of the respective amino and methylamino groups of 3-O-demethylistamycin B$_O$. Alternatively, 1,2',6'-tri-N-protected 3-O-demethylistamycin B$_O$ of formula III may be obtained in a higher yield by reacting 3-O-demethylistamycin B$_O$ with one molar equivalent of a divalent cation such as those of divalent transition metals such as copper, nickel and cobalt and of zinc (II) to form a metal complex, and reacting the complex with 3-5 moles of an amino-protecting group-introducing reagent, followed by removal of the metal cation from the reaction product (see, for example, published U.K. Patent Application No. 2,036,020).

The subsequent glycylation (i.e. acylation with glycine) of the 4-methylamino group of the 1,2',6'-tri-N-protected 3-O-demethylistamycin B$_O$ of formula III may be effected by reacting the compound with glycine or a reactive derivative thereof in accordance with any of the known N-acylation processes for peptide-syntheses such as the dicyclohexylcarbodiimide process, mixed acid anhydride process, azide process, active ester process, etc. The reaction may be conducted over a temperature range of from about 0° C. to about 100° C. in a solvent such as methanol, dioxane, acetonitrile or methylene chloride. It is preferable for the glycine reagent to have the amino group protected, and the amino-protecting group for this purpose may be the same as or different from those on the 1- and 2'-amino groups and on the 6'-methylamino group of 3-O-demethylistamycin B$_O$ and which is easily removable. Thus, the amino-protecting group for protecting the amino group in the glycine reagent may be selected from the abovementioned amino-protecting groups and some divalent amino-protecting groups such as those of a Schiff base type. The acylation reaction with a glycine reagent is preferably carried out according to an active ester process in an organic solvent such as dioxane under heating to a temperature of 40°-60° C., thus giving a compound of formula IV above.

The removal of the amino-protecting groups on the amino and methylamino groups of the compound of formula IV may be effected in a known manner, for example, by hydrogenolysis in the presence of palladium, platinum oxide, etc. as catalyst for the removal of an aralkyloxycarbonyl group or by hydrolysis in an aqueous solution of trifluoroacetic acid, acetic acid, etc. or a diluted aqueous acid solution such as a diluted hydrochloric acid for the removal of other amino-protecting groups.

3-O-Demethyl-2''-N-formimidoylistamycin B of formula Ic:

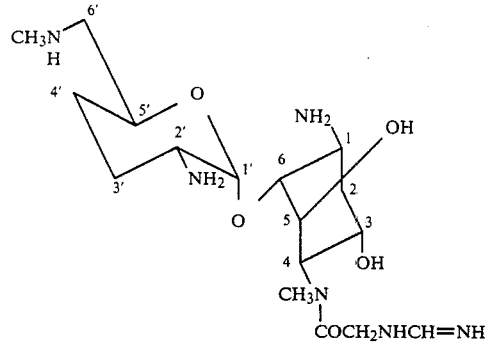

may be prepared according to this invention by formimidoylating the 2''-amino group of 3-O-demethylistamycin B of formula Ib. Thus, for this purpose, a 1-, 2'- and 6'-tri-N-protected derivative of 3-O-demethylistamycin B$_O$ of formula III above is provided as starting material. The compound of Formula III is reacted with a conventionally N-protected glycine whose amino-protecting group is different from those on the 1-, 2'- and 6'-positions of the compound of Formula III, or with a reactive derivative thereof, to acylate the 4-methylamino group, thus forming a compound of Formula V:

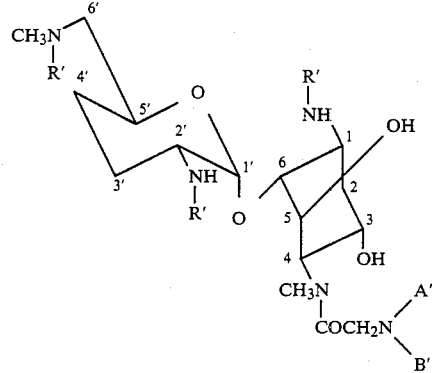

wherein R' represents a conventional monovalent amino-protecting group, A' represents a hydrogen atom and B' represents a conventional monovalent amino-protecting group which is different from R', or A' and B' together form a conventional divalent amino-protecting group. Then, the amino-protecting group on the 2''-amino group in the glycine moiety of the compound of Formula V is selectively removed and the resulting compound is reacted with an iminoether to convert the 2''-amino group into an amidine group, thus forming a compound of formula VI:

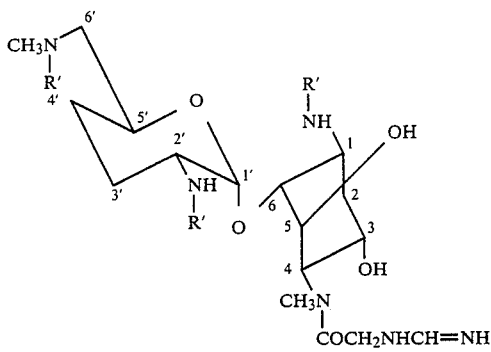

(VI)

wherein R' has the same meaning as defined above. Finally, the remaining amino-protecting groups on the 1-, 2'- and 6'-positions of the compound of formula VI are removed to yield 3-O-demethyl-2''-N-formimidoylistamycin B of formula Ic.

In one preferred example for forming an N-protected intermediate compound of formula V wherein R' is benzyloxycarbonyl group, A' is hydrogen and B' is tert-butoxycarbonyl group, 1,2',6'-tri-N-benzyloxycarbonyl-3-O-demethylistamycin $B_O$ is acylated on the 4-methylamino group with the N-hydroxysuccinimide ester of N-tert-butoxycarbonylglycine. According to another preferred embodiment, 1,2',6'-tri-N-tert-butoxycarbonyl-3-O-demethylistamycin $B_O$ is acylated on the 4-methylamino group with the N-hydroxysuccinimide ester of N-benzyloxycarbonylglycine, thus forming an N-protected intermediate compound of formula V in which R' is tert-butoxycarbonyl, A' is hydrogen and B' is benzyloxycarbonyl group.

In the formimidoylation step, the iminoether reagent to be used may be one having the general formula:

R''OCH=NH wherein R'' represents a lower alkyl group or an aralkyl group such as benzyl, or an acid addition salt thereof such as the hydrochloride or sulfate. The use of an iminoether hydrochloride such as ethylformimidate hydrochloride or benzylformimidate hydrochloride is preferred. The reaction may be conducted in an organic solvent such as dioxane or methanol or in an aqueous solution at a temperature of below about 30° C. in a known manner. The resulting compound of formula VI, 1,2',6'-tri-N-protected-3-O-demethyl-2''-N-formimidoylistamycin B, or an acid addition salt thereof, may be purified by a column chromatography using a silica gel or the like.

The remaining amino-protecting groups on the 1- and 2'-amino groups and on the 6'-methylamino group of the compound of formula VI may be removed by a known method as above-mentioned, thus to yield the desired 3-O-demethyl-2''-N-formimidoylistamycin B of formula Ic.

3-O-Demethylistamycin B and 3-O-demethyl-2''-N-formimidoylistamycin B of this invention have a high antibacterial activity and are of a low toxicity to animals. Accordingly, these compounds are useful similarly to the known antibacterial antibiotics and may be formulated into known pharmaceutical forms and administered in the same manner as the known antibacterial antibiotics. According to a further aspect of this invention, there is provided a pharmaceutical composition comprising an antibacterially effective amount of 3-O-demethylistamycin B or 3-O-demethyl-2''-N-formimidoylistamycin B, or a pharmaceutically acceptable acid addition salt thereof, in combination with a pharmaceutically acceptable carrier. It will be appreciated that the actual preferred dosages of the active new compounds of this invention used will vary according to the particular compound being used, the particular composition formulated, the mode of application and the particular situs and organism being treated. Many factors that modify the action of the drug will be taken into account by the skilled in the art, for example, age, body weight, sex, diet, time of administration, route of administration, rate of excretion, drug combinations, reaction sensitivities and severity of the disease. Optimal application rates for a given set of conditions can be ascertained by the skilled in the art using conventional dosage determination tests in view of the above guidelines.

The following Examples further illustrate the preparation of the compounds according to this invention.

EXAMPLE 1

Preparation of 3-O-demethylistamycin $B_O$

Istamycin $B_O$. monocarbonate (500 mg, 1.27 mmol) was dissolved in 48% hydrobromic acid (50 ml) and the solution was heated in a sealed tube at 90°–93° C. for 4 hours. The reaction solution was concentrated to dryness in vacuo and the residue was dissolved in water (50 ml). The solution was adjusted to pH 8.5 with addition of 7M aqueous ammonia and passed through a column (21×550 mm) of 200 ml of CM-Sephadex C-25 (NH4-form, a product of Pharmacia Co., Sweden). The column was eluted gradiently with 0.15M aqueous ammonia (1120 ml) and 0.70M aqueous ammonia (1120 ml). The eluate was collected in 16 ml-fractions. The fractions Nos. 85 to 102 were combined together and concentrated to dryness in vacuo to afford 275 mg of a colorless powder of 3-O-demethylistamycin $B_O$.dicarbonate. Yield 49%.

EXAMPLE 2

Preparation of 3-O-demethylistamycin B

3-O-Demethylistamycin $B_O$.dicarbonate (150 mg, 0.34 mmol) obtained in Example 1 was dissolved in methanol (12 ml) and to the solution N-benzyloxycarbonyloxysuccinimide (329 mg, 1.34 mmol) was added over 2 hours with stirring and under cooling to −10° C., and the mixture was stirred for further two hours. The reaction solution was concentrated in vacuo to form a syrup, which was then dissolved in chloroform (25 ml). The solution was washed with water (8 ml×2) and the chloroform layer was dehydrated over anhydrous sodium sulfate and concentrated to dryness in vacuo to yield a crude powder of 1,2',6'-tri-N-benzyloxycarbonyl-3-O-demethylistamycin $B_O$. This powder was dissolved in dioxane (9 ml) and to the solution were added triethylamine (0.5 ml) and N-(N-benzyloxycarbonylglycyloxy)succinimide (250 mg, 0.82 mmol), and the mixture was heated to 55° C. for 2 hours under stirring. The reaction solution was concentrated in vacuo and the residue was dissolved in chloroform (25 ml) and washed with water (8 ml×2). The chloroform layer was dehydrated over anhydrous sodium sulfate and concentrated to dryness in vacuo to give a crude powder (389 mg). This powder was purified by column chromatography on silica gel (30 g of Wako gel C-200, a product of Wako Pure Chemical Industries, Ltd., Japan; the column size: 14×350 mm) developed with a mixture of ethyl acetate-toluene (5:2 by volume) to afford a colorless powder (83 mg) of 1,2',6',2''-tetra-N-benzyloxycarbonyl-3-O-demethylistamycin B. This powder was dissolved in a mixture of methanol (5 ml), water (1 ml) and acetic acid (0.5 ml) and the solution was subjected to hydrogenolysis under a hydrogen stream in the presence of 5% palladium-carbon (15 mg; a product of Kawaken Fine Chemical Company, Japan) as catalyst at room temperature for 1.5 hours. After the catalyst was removed by filtration, the reaction solution was concentrated to dryness in vacuo to yield a crude powder (60.9 mg). A 60 mg portion of the powder was dissolved in water (3 ml) and the solution was adjusted to pH 8 with addition of aqueous ammonia and passed through a column (8×95 mm) of 5 ml of Amberlite CG-50 (NH$_4$ form, a product of Rohm & Haas Co., U.S.A.). The column was washed with water (10 ml) and then eluted with 0.2M aqueous ammonia (70 ml) and 0.8M aqueous ammonia (70 ml) in a manner of gradient elution. The eluate was collected in 1.4 ml-fractions. The fractions Nos. 22–38 were combined together and concentrated to dryness in vacuo to afford a colorless powder (35.5 mg) of 3-O-demethylistamycin B.sesquicarbonate. Yield: 23%.

EXAMPLE 3

Preparation of 3-O-demethyl-2''-N-formimidoylistamycin B

3-O-Demethylistamycin B$_O$.dicarbonate (260 mg, 0.59 mmol) obtained in Example 1 was dissolved in methanol (24 ml) and to the solution were added triethyl amine (0.32 ml) and 2-(tert-butoxycarbonyloxyimino)-2-phenylacetonitrile (433 mg, 1.76 mmol) (BOC-ON, a product of Aldrich Co., U.S.A.) under stirring and cooling (0°–8° C.), and the mixture was allowed to stand overnight. The reaction solution was concentrated in vacuo and then dissolved in chloroform. The chloroform solution was purified by column chromatography on silica gel (20 g of Wako gel C-200; the column size: 14×250 mm). The column was washed with chloroform (80 ml) and developed with a mixture of chloroform-methanol (10:1 by volume), and the eluate was concentrated to dryness to afford a colorless powder (255 mg) of 1,2',6'-tri-N-tert-butoxycarbonyl-3-O-demethylistamycin B$_O$. Yield: 66%.

This powder (215 mg, 0.33 mmol) was dissolved in dioxane (7 ml) and there were added to the solution triethylamine (0.072 ml) and N-(N-benzyloxycarbonyl-glycyloxy)succinimide (160 mg, 0.52 mmol), and the mixture was maintained at 55° C. for 2 hours to hasten the reaction. The reaction solution was concentrated in vacuo and purified by column chromatography on silica gel (26 g of Wako gel C-200; the column size: 14×310 mm) developed with a mixture of ethyl acetate-toluene (11:4) to yield a colorless powder (197 mg) of 2''-N-benzyloxycarbonyl-1,2',6'-tri-N-tert-butoxycarbonyl-3-O-demethylistamycin B. Yield: 75%.

This powder (190 mg, 0.23 mmol) was dissolved in a mixture of methanol (6 ml), water (1 ml) and acetic acid (0.05 ml) and the solution was subjected to hydrogenolysis in a hydrogen stream in the presence of 5% palladium-carbon (30 mg) as catalyst at room temperature for 3 hours. After the catalyst was removed by filtration, the reaction solution was concentrated to dryness in vacuo to afford a colorless powder (160 mg) of 1,2',6'-tri-N-tert-butoxycarbonyl-3-O-demethylistamycin B.monoacetate. Yield: 93%.

This powder (150 mg, 0.20 mmol) was dissolved in a mixture of methanol (27 ml) and water (4 ml), and to the solution there was added dropwise over 15 minutes a solution of benzylformimidate hydrochloride (209 mg, 1.22 mmol) in methanol (5 ml) under ice-cooling, while the pH of the reaction solution was adjusted to 8.0–8.5 by addition of a 0.5N potassium hydroxide. The reaction solution was further stirred for 30 minutes under ice-cooling, then adjusted to pH 4.0 by addition of 1N hydrochloric acid and concentrated in vacuo to give a syrup. The syrup was dissolved in butanol (50 ml) and the solution was washed with water (25 ml×2). The butanol layer separated was concentrated to dryness in vacuo and the residue was purified by column chromatography on silica gel (20 g of Wako gel C-200; the column size: 12×370 mm) developed with a mixture of chloroform-methanol (4:1 by volume) to yield a colorless powder (63 mg) of 1,2',6'-tri-N-tert-butoxycarbonyl-3-O-demethyl-2''-N-formimidoylistamycin B. Yield: 42%.

This powder (63 mg) was dissolved in a 90% trifluoroacetic acid (2.5 ml) and the solution was allowed to stand for 1.5 hours and then concentrated to dryness in vacuo. The residue was dissolved in water (2 ml) and the solution was passed through a column (8×10 mm) of 5 ml of Amberlite IRA-400 (SO$_4$ form; a product of Rohm & Haas Co., U.S.A.) to effect a salt exchange. The effluent (6 ml) was concentrated to dryness in vacuo to obtain a colorless powder (53 mg) of 3-O-demethyl-2''-N-formimidoylistamycin B.disulphate.trihydrate. Yield: 95%.

We claim:

1. A 3-O-demethyl derivative of a compound of the istamycin B series, having the formula

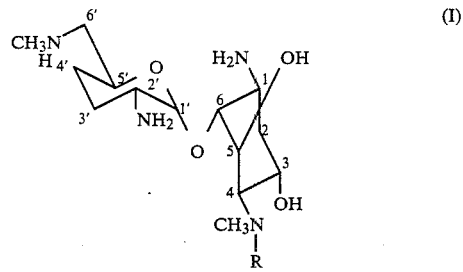

wherein R represents a hydrogen atom, a glycyl group or an N-formimidoylglycyl group, or an acid addition salt or salt-hydrate thereof.

2. The compound of claim 1 wherein R represents a hydrogen atom, which is designated 3-O-demethylistamycin B$_O$, or an acid addition salt or salt-hydrate thereof.

3. The compound of claim 1 wherein R represents a glycyl group, which is designated 3-O-demethylistamycin B, or an acid addition salt or salt-hydrate thereof.

4. The compound of claim 1 wherein R represents an N-formimidoylglycyl group, which is designated 3-O-demethyl-2''-N-formimidoylistamycin B, or an acid addition salt or salt-hydrate thereof.

5. A pharmaceutical composition comprising an antibacterially effective amount of 3-O-demethyl-2''-N-formimidoylstamycin B as defined in claim 4 or a pharmaceutically acceptable acid addition salt or salt-hydrate thereof, in combination with a pharmaceutically acceptable carrier.

* * * * *